(12) United States Patent
Sussman

(10) Patent No.: US 6,626,667 B2
(45) Date of Patent: Sep. 30, 2003

(54) IMPLANT GUIDE ARRANGEMENT

(76) Inventor: Harold I. Sussman, 64 Popham Rd., Scarsdale, NY (US) 10583

( * ) Notice: Subject to any disclaimer, the term of this patent is extended or adjusted under 35 U.S.C. 154(b) by 0 days.

(21) Appl. No.: 10/047,962

(22) Filed: Jan. 16, 2002

(65) Prior Publication Data

US 2003/0134252 A1 Jul. 17, 2003

(51) Int. Cl.$^7$ .................................. A61C 3/02
(52) U.S. Cl. ............................ 433/76; 606/96
(58) Field of Search .................. 433/72, 75, 76; 606/96

(56) References Cited

U.S. PATENT DOCUMENTS

| | | | |
|---|---|---|---|
| 3,254,413 A | | 6/1966 | Suga |
| 3,380,163 A | | 4/1968 | Westerman |
| 4,325,373 A | * | 4/1982 | Slivenko et al. |
| 4,344,755 A | | 8/1982 | Gold et al. |
| 5,302,122 A | * | 4/1994 | Milne ........................ 433/76 |
| 5,741,133 A | * | 4/1998 | Gordils et al. ............. 433/76 |
| 5,833,693 A | * | 11/1998 | Abrahami .................. 606/96 |
| 5,842,859 A | * | 12/1998 | Palacci ...................... 433/72 |
| 5,888,065 A | | 3/1999 | Sussman |
| 6,062,856 A | | 5/2000 | Sussman |
| 6,319,006 B1 | | 11/2001 | Scherer et al. |
| 6,537,067 B1 | * | 3/2003 | Wennemann ............... 433/76 |

FOREIGN PATENT DOCUMENTS

DE   196 05 394 A1  * 10/1996
WO   WO 01/34055 A1  * 5/2001

OTHER PUBLICATIONS

"Tooth Devitalization Via Implant Replacement: A Case Report" H. I. Sussman, Periodontal Clinical Investigations, vol. 20, No. 1, 1998, pp. 22–24.
"Simplified Guide for Precise Implant Placer: A Technical Note" Kennedy, et al, Intl. Journal of Oral . . . Implants, vol. 13, No. 5, 1998, pp. 684–688.
"Positioning Implants for Overdentures: A Prototype . . . ", Walton, Intl. Journal of Oral . . . Implants, vol. 14, No. 2, 1999, pp. 295–297.
Fixture Positioning Guides, Branemark System, Nobel Biocare, 1996 (4 Pgs.).

* cited by examiner

*Primary Examiner*—Ralph A. Lewis
(74) *Attorney, Agent, or Firm*—Notaro & Michalos P.C.

(57) ABSTRACT

A dental implant guide arrangement accurately guides a bur for drilling a pilot or initial hole for a dental implant into the upper or lower jaw bone of an edentulous (toothless) patient. The arrangement includes jaws, pointed projections or other jaw bone ridge engagement structures which engage the ridge area of the upper or lower jaw bone to fix the arrangement in place. A preferably closed cylindrical guide channel is connected to the engagement structure and extends outwardly along and over the jaw bone ridge. The axis of the channel is parallel to an acceptable axis for the pilot or initial hole into the ridge. The bur can be guided along the guide channel for accurately drilling the hole. Another part of the arrangement is used after the initial hole is drilled to accurately space and orient subsequent implant hole in the jaw bone.

18 Claims, 6 Drawing Sheets

IMPLANT GUIDE ARRANGEMENT

FIELD AND BACKGROUND OF THE INVENTION

The present invention relates in general to dental implants, and in particular to a new and useful dental implant hole guide arrangement which provides a dentist with an accurate guide to follow for drilling the critical initial pilot hole for a dental implant into an edentulous or toothless jaw bone ridge, so that the hole is aligned on an acceptable axis in the patient's jaw bone.

Since 1981, dental root form implants have become a standard procedure for replacing missing teeth. Unlike other dental procedures such as crown and bridge work, root canals and the like, which utilize at least part of the original tooth as a foundation for the tooth replacement, implants require the drilling of holes directly into the bone of the jaw.

Although the dental implants have many benefits, particularly where a patient is missing teeth over large portions of the mouth, various complications can follow implant placement, especially to adjacent teeth. The bone may be overheated during implant surgery for example and this can devitalize an adjacent tooth. Endodontic lesions can also form which compromise the implant fixture by preventing integration of the bone around the fixture (Osseointegration) causing loss of the implant.

Another problem involves patient with no teeth or so called edentulous patients.

Within the confines of the mouth, it is very difficult to accurately align a dental bur for drilling the crucial initial pilot hole of about 2 mm in diameter. The pilot hole must be drilled along an acceptable axis into the jaw bone which both avoids any critical structures in the bone such as nerves, blood vessels and the like, but also avoids intersecting the root of an adjacent tooth which may not be apparent without x-rays. Even with x-rays, however, it is difficult for a dentist to accurately align the bur without some help.

U.S. Pat. No. 5,888,065, invented by the present inventor, discloses a dental implant guide arrangement that is capable of accurately guiding a bur for drilling a pilot hole for a dental implant. The arrangement includes a pair of jaws which engage lingual and buccal surfaces of a tooth and are held to each other by a fixing mechanism, such as a screw. A guide member extends from one of the jaws and has a semi-cylindrical guide that is parallel to an acceptable axis for the pilot hole. The bur can be guided along the guide for accurately drilling the pilot hole.

A limitation of the invention in U.S. Pat. No. 5,888,065, however, is that the patient must have at least one tooth adjacent each area selected to receive an implant. Since it is customary to install from one to three implants in each quadrant of a patients mouth if natural tooth structures are not present, this poses a difficult problem for patients with no teeth.

One very complex and time consuming technique for properly aligning the initial implant hole for a patient is disclosed in U.S. Pat. No. 5,015,183 entitled LOCATING DEVICE AND METHOD OF PLACING A TOOTH IMPLANT. According to this method, a stent comprising a negative impression of a patient's teeth in the vicinity of the implant is taken. Multiple x-ray opaque strips are placed in the negative impression and an oblique x-ray is taken. This x-ray is used as a diagnostic tool for the patient's jaw structure to help plot the trajectory of an implant fixture in the jaw.

Another problem associated with the use of a stent is that when a surgical stent is fabricated from an alginate jaw impression, as is commonly done, the registration of the surface jaw tissue does not always reflect the underlying topography of the jaw bone where the implant is to be placed.

In any case, once an acceptable initial implant hole is formed in the jaw, subsequent holes can be produced by using the initial hole as a guide. This is when multiple implants are to be installed. See, for example, U.S. Pat. Nos. 5,741,133 and 5,302,122. Other techniques and apparatuses for drilling holes in the jaw bone are disclosed in U.S. Pat. Nos. 4,787,848 and 4,998,881. A need remains, however, for a simple and effective tool which can be used particularly by general dentists to permit them to produce the initial pilot hole along an acceptable axis in a patient's jaw bone. Once the initial bore is made, it can be enlarged to the required final diameter, generally about 4 mm, using ever increasing bur sizes. Once the initial hole is drilled, the enlargements are easily made using the initial hole as the guide. The present invention provides a way of making that critical initial hole.

SUMMARY OF THE INVENTION

The present invention is used to drill a first, properly aligned pilot hole for an implant or the first implant hole itself, for the upper and/or lower jaws of edentulous patients. It is conventional to drill an initial small diameter hole of about 2 mm, followed by enlarging the hole until the appropriate size for the implant is reached. This is done using different burs of ever increasing diameter until a final hole diameter of about 4 mm is reached.

According to the present invention, a device having a guide to align the first pilot hole is provided. Guides are not necessary for the subsequent enlarging holes since the original pilot hole serves as a guide for drilling the subsequent holes.

The invention solves the serious prior art problem of improperly aligned implant holes in edentulous patients.

Accordingly, an object of the present invention is to provide an implant guide arrangement for use in drilling a hole in an edentulous jaw bone in preparation for receiving a dental implant in the jaw bone, comprising bone engagement means adapted to engage a jaw bone ridge area adjacent a site on a patients jaw bone ridge for receiving the hole, the bone engagement means being adapted to fix the arrangement on the ridge; and a guide member connected to the bone engagement means and adapted to extend from the bone engagement means over the site, the guide member having a guide channel which has an axis that is aligned with an acceptable axis of the hole to be drilled, the guide channel being shaped to guide a bur for drilling the hole.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
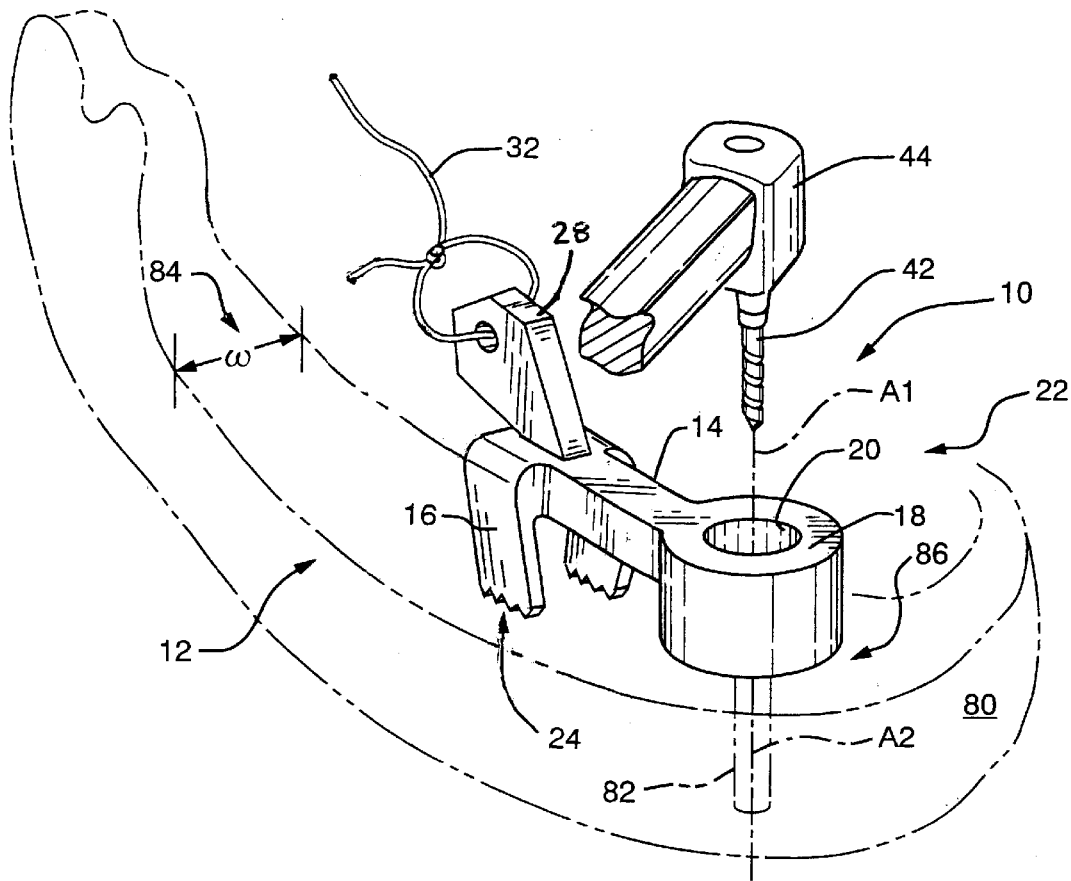
FIG. 1 is a perspective view of a first embodiment of the present invention shown engaged onto an edentulous lower jaw bone ridge to anchor the guide arrangement for accurately guiding a handpiece bur for drilling the first implant hole or implant pilot hole in the ridge.

Referring now to the drawings, in which like reference numerals are used to refer to the same or similar elements, FIG. 1 shows an implant guide arrangement 10 for use in drilling a hole in an edentulous lower jaw bone 80, in preparation for receiving a dental implant in the jaw bone. The hole may be a small diameter pilot hole 82 or a full diameter hole for receiving an implant.

The arrangement 10 includes bone engagement means 12 adapted to engage a jaw bone ridge area 84, adjacent a site 86 on a patients jaw bone ridge for receiving the hole 82. The bone engagement means 12 is adapted to fix the arrangement 10 on the ridge or at the ridge area 84, 86.

The invention is used after the practitioner has sectioned and retracted the gingiva or gum, at least in the areas 84 and 86 of the jaw bone 80. The ridge 84 of a patient usually has a width W of about 6 to 10 mm and is substantially flat on top. If, in any particular patient the ridge is not flat the practitioner can flatten the ridge using an appropriate bone cutting tool.

The arrangement also includes a guide member 22 connected by a bridge 14, to the bone engagement means 12 and adapted to extend from the bone engagement means over the site 86. The guide member 22 has a guide channel 20 defined through a cylindrically portion 18 of the guide member 22, which has an axis A1 that is aligned with an acceptable axis A2 of the hole 82 to be drilled, e.g. by the bur 42 of a dental handpiece 44. The guide channel is shaped to guide the bur for drilling the hole 82 and is preferably a closed circle 20 to positively guide the bur along the axes A1 and A2.

Figure 2:
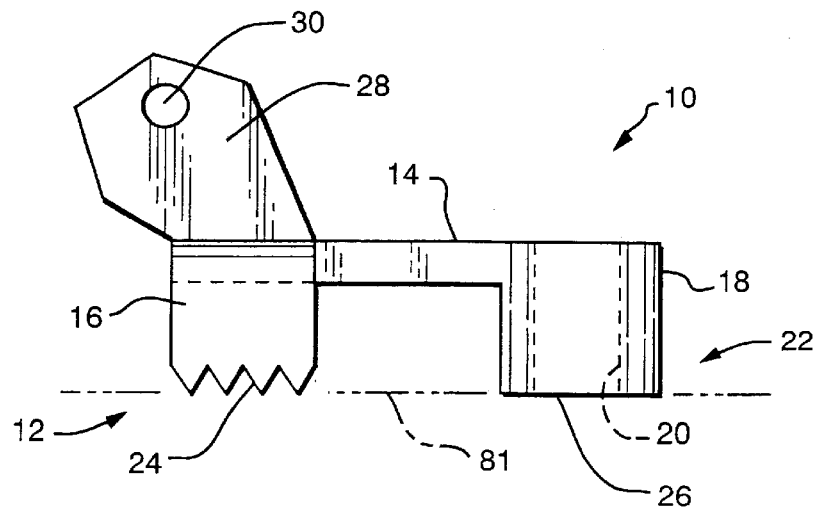
FIG. 2 is a side view thereof.

In the embodiment of FIGS. 1 and 2, bone engagement means 12 is in the form of a pair of spaced apart projections 16 extending substantially parallel to the guide channel axis A1, each projection having a toothed, bone engaging bottom surface 24 for engaging the ridge of a jaw bone.

The teeth on surface 24 may be triangular as shown, or have other shapes or be roughened or knurled. The teeth or roughening or knurling should, however, be sharp enough to at least slightly bite into the bone ridge and anchor the arrangement against lateral motion. The toothed or rough surface 24 must also be substantially in the same plane 81 as the bottom, ridge engaging surface 26 of the guide cylinder 18, so that when the teeth of surface 24 are engaged onto the ridge 84 with channel 20 aligned with the hole 82 to be drilled, the channel axis A1 is fully aligned with and parallel to the hole axis A2. Surface 26 may also be roughened, knurled or the like to help fix the device on the jaw bone, or may be smooth, in which case the fixing effect of the surface 24 is relied on.

A holding tab 28 is formed over projections 16 and contains a hole 30 for receiving dental floss or other sterile, strong string 32. This helps avoid losing the arrangement in the patients mouth and the tab gives the practitioner a hand-hold on the arrangement to keep it well placed against the jaw bone while the practitioner's other hand holds the handpiece to drill the properly aligned hole 82.

Figure 7:
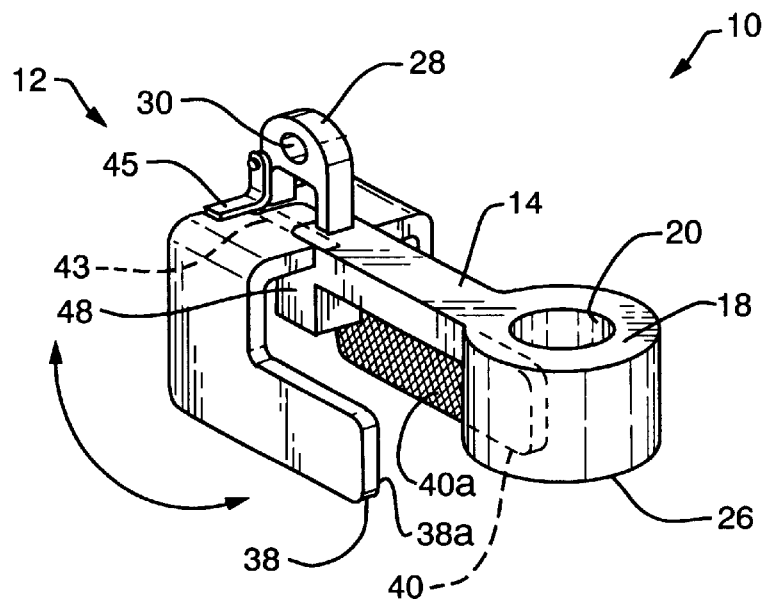
FIG. 7 is a perspective view of another embodiment of the invention for the lower jaw of a patient.
Figure 8:
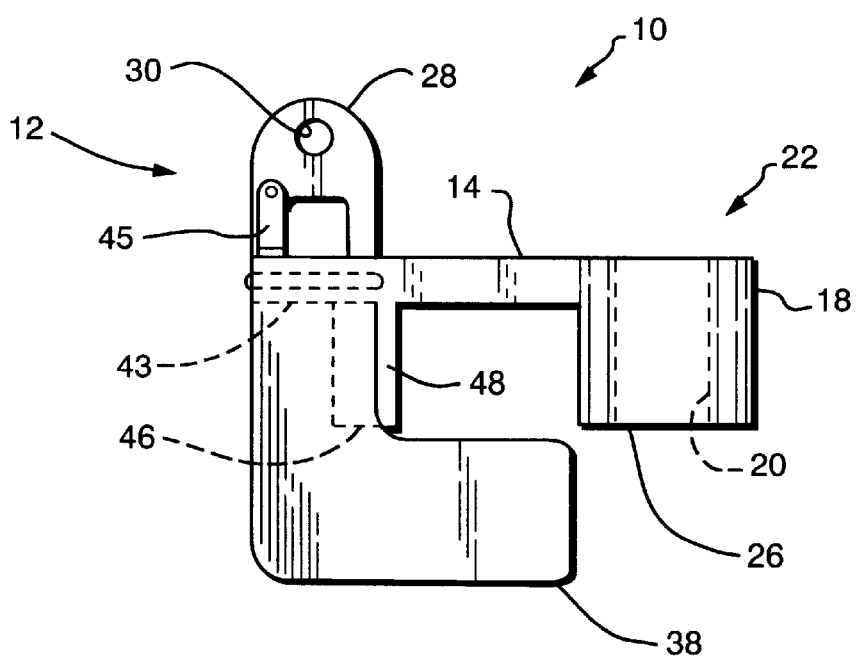
FIG. 8 is a side view of the embodiment of FIG. 7.

FIGS. 3, 4, 7 and 8 illustrate two further embodiments of the invention where the bone engagement means 12 comprises a pair of jaws 34 and 36 in FIGS. 3 and 4, and 38 and 40 in FIGS. 7 and 8. At least one of the jaws in each pair is articulated with respect to the other and the jaws are positioned and shaped to engage respective buccal and lingual surfaces of the ridge area of a jaw bone for engaging the jaw bone and fixing the guide member 22 over the ridge of the jaw bone.

These two embodiments also include means defining a reference surface 46 for engaging the ridge area, which reference surface 46 is substantially in a common plane with the bone engagement surface 26 of the guide member 22 to insure that the axis A1 if the channel 20 is aligned with the axis A2 of the hole to be drilled. Surface 46 is defined on a downward projection 48 formed under bridge 14, near the jaws.

Figure 3:
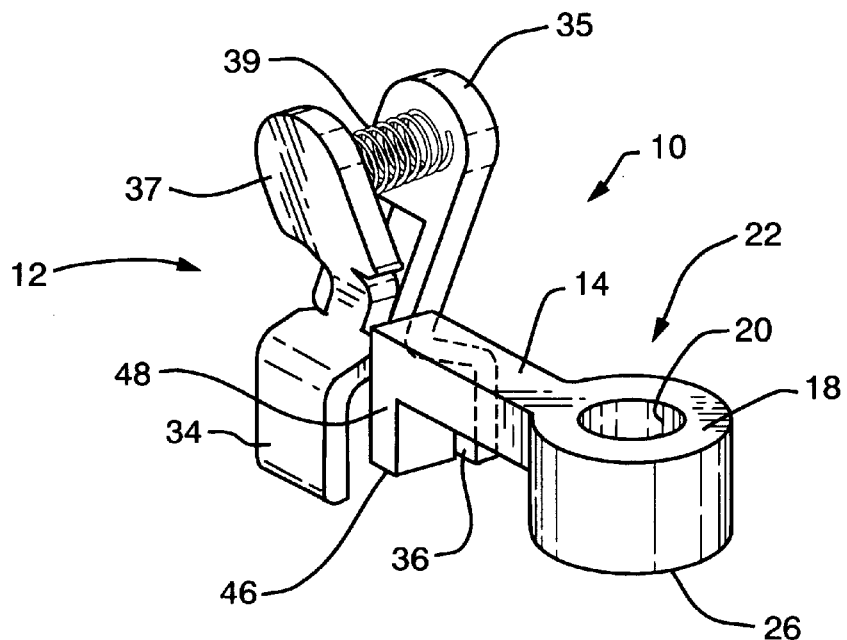
FIG. 3 is a perspective view of another embodiment of the invention with a clamping device to free the dentist's other hand.
Figure 4:
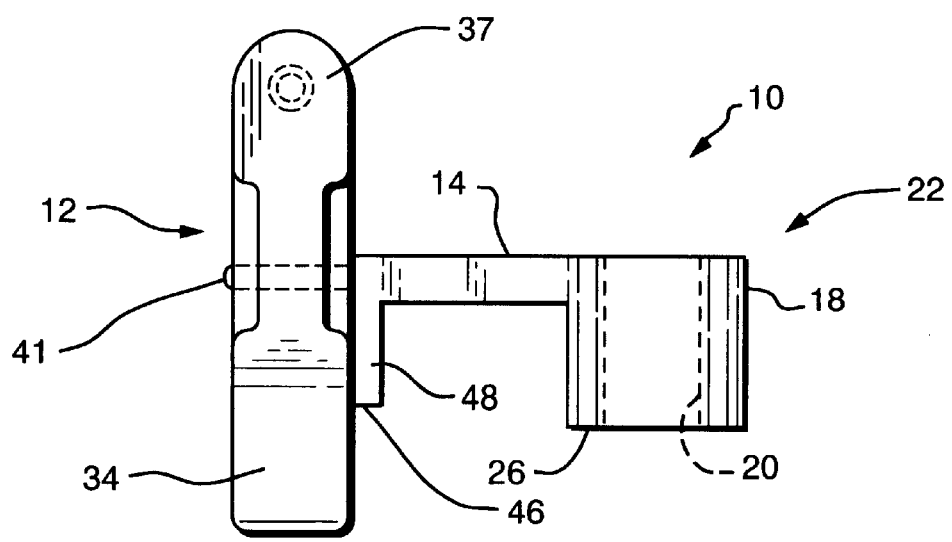
FIG. 4 is a side of the embodiment of FIG. 3.

In the embodiment of FIGS. 3 and 4, jaws 34, 36 each have upper ends or activation arms 35, 37 which can be squeezed together for separating jaws 34, 36. The arms are pivotally connected to each other at a hinge formed by a pin 41 extending outwardly from bridge 14 as shown in FIG. 4. Thus, in scissors-fashion, the practitioner can squeeze arms 35, 37 together to open jaws 34, 36. In this position, the arrangement is dropped down over the ridge area of a jaw bone. Arms 35, 37 are then released and are spread apart by a spring 39 to squeeze jaws 34, 36 together to firmly embrace the ridge area of the jaw bone. This anchors the arrangement while the coplanar relationship between surfaces 26, 46 keeps the channel 20 aligned with the location of the hole to be drilled.

In the embodiment of FIGS. 7 and 8, only jaw 38 is pivotally mounted at a hinge 43 to the bridge 14. Jaw 40 is fixed to or made as one piece with bridge 14. Both jaws 40 and 38 have inner bone facing surfaces that can be roughened, toothed or ridged to better engage the surface of the bone. Similar treatment can be provided on the facing surfaces of jaws 34 and 36 in the embodiments of FIGS. 3 and 4.

As evident in the embodiment of FIGS. 7 and 8, each jaw also includes a lateral projection 38a, 40a, which extends toward the guide member 22, but along the surfaces of the jaw bone to help better embrace the ridge and anchor the arrangement.

As with the embodiment of FIGS. 1 and 2, a tab or handle 28 with thread-receiving hole 30 is included in the embodiment of FIGS. 7 and 8. Handle 28 is centered with cylinder 18 and between the jaws 38, 40 to help the dentist properly align the guide bore 20 over the jaw bone.

A spring, for example, a strong flat leaf spring bent into an L-shape 45, is also fixed at one end to the handle 28 or to the top of bridge 14 and extends, in cantilever fashion, over the top of jaw 38, to help bias the jaw toward the jaw bone. The double arrow in FIG. 7 shows the movement of jaw 38.

Figure 5:
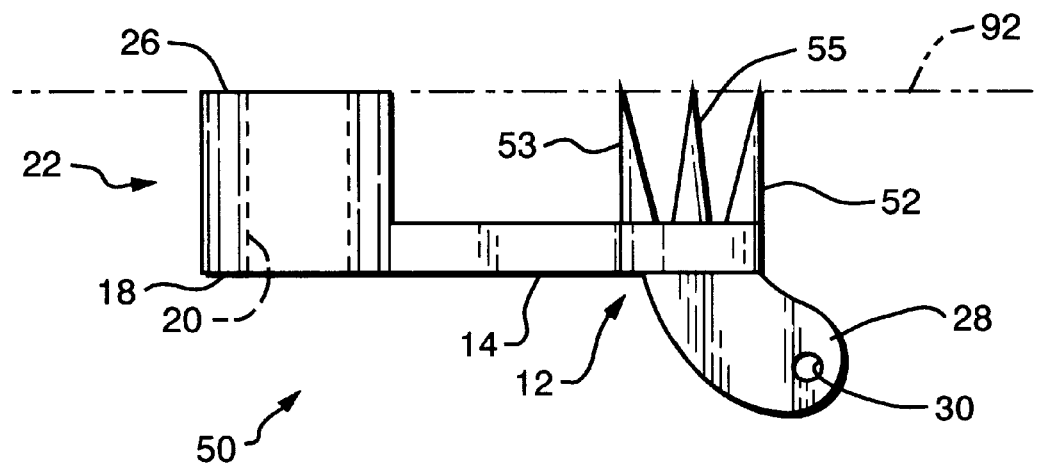
FIG. 5 is a side view of an embodiment of the invention for guiding the drilling of the initial hole in the upper jaw bone of a patient.
Figure 6:
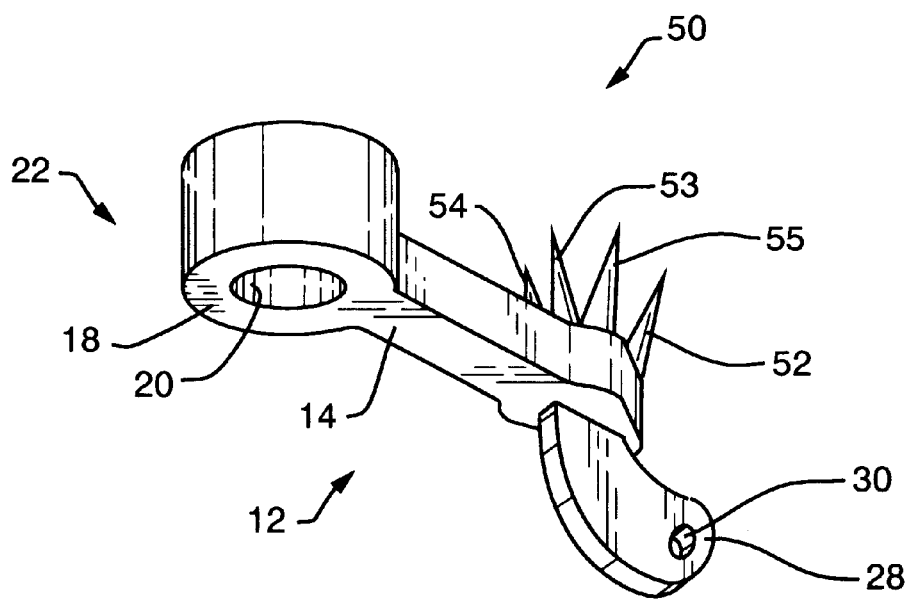
FIG. 6 is a perspective view of the embodiment of FIG. 5.

Although the embodiments of FIGS. 1, 2, 3, 4, 7 and 8 can be used both for an upper jaw and a lower jaw, the upper jaw generally provides the practitioner with less room and is more difficult to work on. For this reason, the inventor has provided the embodiment of FIGS. 5 and 6, which is especially designed for an upper jaw bone 90 having a ridge surface 92. As with the other embodiments of the invention, the arrangement 50 of FIGS. 5 and 6 includes a bone engaging means 12, a guide member 22 and a bridge 14 connected therebetween. Guide member 22 comprises a cylindrical guide 18 defining an inner cylindrical channel 20 with an axis meant to align with the axis of the hole to be drilled. A handle 28 with hole 30 is fixed to bridge 14 to give the dentist a hand-hold as with the other embodiments of the invention.

Bone engaging means comprises a flat extension of bridge 14 with a plurality, preferably four equally spaced spikes 52, 53, 54 and 55. The pointed tips of the spikes are positioned to lie substantially in a common plane with the upper surface 26 of dyed cylinder 18. This surface substantially corresponds to the ridge surface 92, again, to accurately anchor the arrangement to the bone with the channel 20 over the site meant for receiving the drilled hole. The four pointed spikes 52, 53, 54 and 55 advantageously incline away from each other to provide maximum stability for the arrangement. As with the spacing of the projections 16 and the embodiment of FIG. 1, however, the spacing between the side spikes 54 and 53 is selected to be equal to or less than the maximum expected width of a jaw bone which can be from about 6 to about 10 mm. Further, the embodiment of FIGS. 5 and 6 can be used for a lower jaw as well as an upper jaw despite its special design for the upper jaw. Surface 26 may be smooth or rough.

Figure 9:
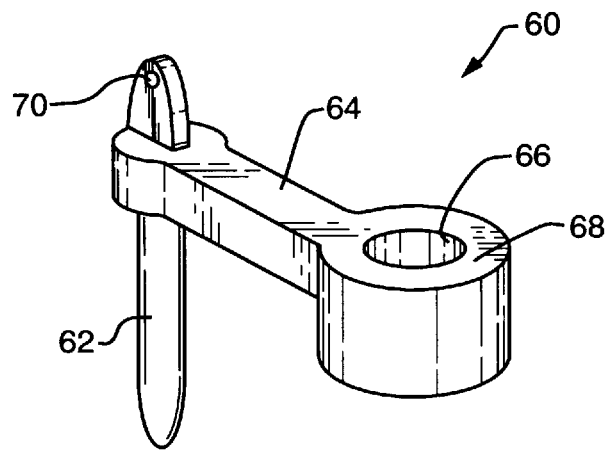
FIG. 9 is a perspective view of a still further embodiment of the invention, for use in guiding the drilling of subsequent implant or pilot holes in the upper or lower jaw of a patient, for use with or without the arrangements of FIGS. 1–8.
Figure 10:
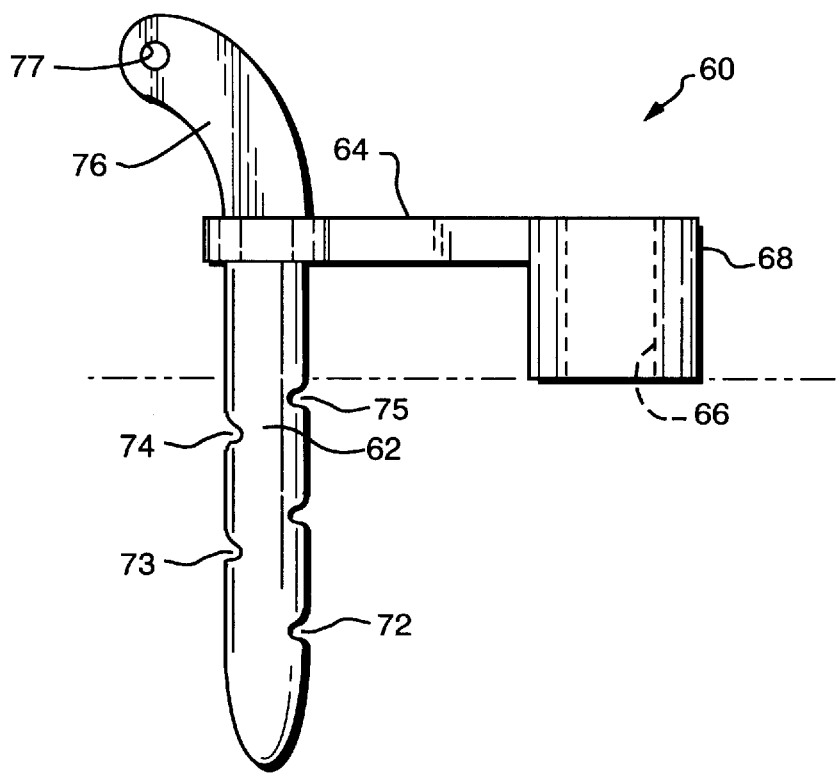
FIG. 10 is a side view of a still further embodiment of the invention for use in guiding the drilling of subsequent implant holes in the upper or lower jaw of a patient, for use with or without the arrangements of FIGS. 1–8.

Once the first pilot or implant hole 82 is drilled, the inventor has provided the structure shown in FIGS. 9 and 10 to help the practitioner accurately form subsequent implant holes.

This dental implant hole guide extension 60 comprises a positioning pin 62 extending from one end of a bridge 64 and a cylindrical guide member 68 containing a cylindrical channel 66. In the embodiment of FIG. 9, an upper projection or handle 70 extends upwardly from bridge 64 to give the practitioner a visual image of the alignment of the pin 62 in the hole that was previously drilled and also to provide a hand-hold. Channel 66 is positioned by selecting the proper length of bridge 64 to locate the next hole for the next adjacent implant. Generally, 2 or 3 implants per quarter are provided in a patient, in particular, an edentulous patient.

In the embodiment of FIG. 10, pin 62 contains notches or grooves 72, 73, 74 and 75 which can be used to determine the proper depth of the drilled hole. A tab 76 is also provided for holding the extension and contains a hole 77 for thread or string. Notches 72–75 are, for example, 2 mm apart and can be seen in an X-ray of the jaw bone and bore to help guage that the proper depth has been reached.

Figure 11:
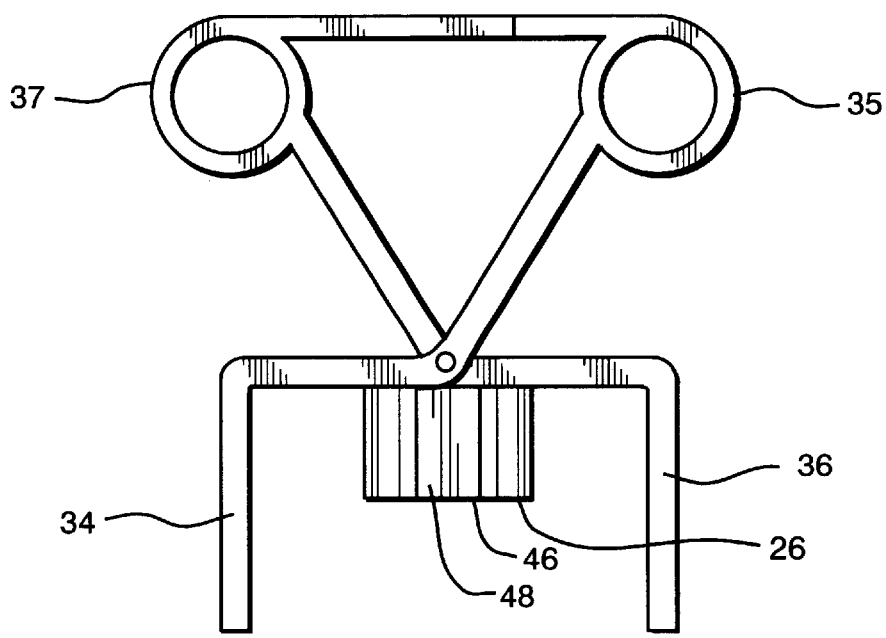
FIG. 11 is an end elevational view of a further embodiment of the invention which uses a hemostat type clamp.
Figure 12:
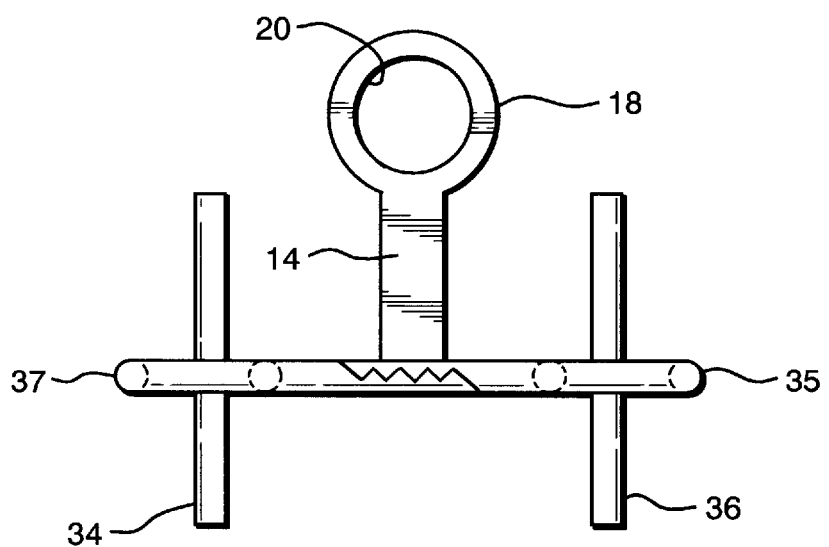
FIG. 12 is a top plan view of the embodiment of FIG. 11

FIGS. 11 and 12 illustrate a further embodiment of the invention where handles 35 and 37 have finger holes and can be squeezed together to clamp the jaws 34 and 36 to the jaw bone ridge area. This squeezed position is maintained by the mated clamping teeth extending from each of the handles like those of a known hemostat. The finger holes are used to also disengage the clamping teeth and release the device from the jaw when the dentist has finished drilling the hole with the help of the guide hole 20 in cylinder 18, which, as in the other embodiments of the invention, is connected to the handles and jaws 34–37 by a bridge 14.

All of the embodiments of the invention can be made of sterilizable surgical steel or other sterilizable metal, which is conventional for medical and dental purposes. The simplicity of structure and few number of parts also improves each embodiments' ability to be sterilized.

While specific embodiments of the invention have been shown and described in detail to illustrate the application of the principles of the invention, it will be understood that the invention may be embodied otherwise without departing from such principles.

What is claimed is:

1. An implant guide arrangement for use in drilling a hole in an edentulous area of a jaw bone in preparation for receiving a dental implant in the jaw bone, comprising:

bone engagement means adapted to engage a jaw bone ridge area adjacent a site on a patients jaw bone ridge for receiving the hole, the bone engagement means being adapted to fix the arrangement on the ridge; and a guide member connected to the bone engagement means and adapted to extend from the bone engagement means over the site, the guide member having a guide channel which has an axis that is aligned with an acceptable axis of the hole to be drilled, the guide channel being shaped to guide a bur for drilling the hole.

2. An arrangement according to claim 1, wherein the guide member defines a closed, cylindrical guide channel.

3. An arrangement according to claim 1, wherein the bone engagement means comprises a pair of spaced apart projections extending substantially parallel to the guide channel axis each projection having a toothed, bone engaging surface for engaging the ridge of a jaw bone, the guide member having a ridge engagement surface which is substantially in a common plane with the toothed, bone engaging surface.

4. An arrangement according to claim 1, wherein the bone engagement means comprises a pair jaws, at least one of the jaws being articulated with respect to the other and the jaws being positioned and shaped to engage respective buccal and lingual surfaces of the ridge area of a jaw bone for engaging the jaw bone and fixing the guide member over the ridge of the jaw bone, and means defining a reference surface for engaging the ridge area, which reference surface is substantially in a common plane with a bone engagement surface of the guide member.

5. An arrangement according to claim 4, including biasing means connected to at least one of the jaws for biasing the jaws together to engage the jaw bone ridge.

6. An arrangement according to claim 5, wherein the biasing means is a spring operatively connected between the jaws.

7. An arrangement according to claim 5, wherein the biasing means is a pair of clamping tooth sets for engaging each other, operatively connected between the jaws.

8. An arrangement according to claim 5, including a bridge connected between the bone engagement means and the guide member, the bone engagement means comprising a pair of arms each carrying one of said jaws, said pair of arms being pivotably connected to each other for movement together to spread the pair of jaws and for movement apart through the action of said biasing means for moving said jaws together.

9. An arrangement according to claim 5, including a bridge connected between said guide member and said bone engagement means, one of said jaws being pivotably mounted to said bridge for movement toward and away from the other of said jaws.

10. An arrangement according to claim 9, including a tab fixed to and extending upwardly from said bridge.

11. An arrangement according to claim 10, including a hole through said tab for receiving thread.

12. An arrangement according to claim 1, including a bridge between said guide member and said bone engagement means, and a plurality of spikes extending outwardly from said bridge at a location spaced from said guide member for engaging a ridge of a jaw bone.

13. An arrangement according to claim 12, when points of said spikes are in a common plane with a surface of the guide member for engaging the bone ridge.

14. An arrangement according to claim 1, including an extension for use with the bone engagement means and guide member, said extension comprising a further guide member, a bridge connected to said further guide member and a pin extending from said bridge, said pin having an axis and said further guide member having a channel with an axis parallel to said axis of said pin and spaced from said axis of said pin by an amount corresponding to a spacing between implant holes to be drilled into the jaw bone ridge.

15. An arrangement according to claim 14, when said further guide member of said extension as a cylindrical hole therethrough.

16. An implant guide arrangement for use in drilling a hole in an edentulous area of a jaw bone in preparation for receiving a dental implant in the jaw bone, comprising, bone engagement means adapted to engage a jaw bone ridge area adjacent a site on a patients jaw bone ridge for receiving the hole, the bone engagement means being adapted to fix the arrangement on the ridge;

a guide member connected to the bone engagement means and adapted to extend from the bone engagement means over the site, the guide member having a guide channel which has an axis that is aligned with an acceptable axis of the hole to be drilled, the guide channel being shaped to guide a bur for drilling the hole, the guide member defining a closed, cylindrical guide channel; and the bone engagement means comprising a pair of spaced apart projections extending substantially parallel to the guide channel axis, each projection having a toothed, bone engaging surface for engaging the ridge of a jaw bone, the guide member having a ridge engagement surface which is substantially in a common plane with the toothed, bone engaging surface.

17. An implant guide arrangement for use in drilling a hole in an edentulous area of a jaw bone in preparation for receiving a dental implant in the jaw bone, comprising:

bone engagement means adapted to engage a jaw bone ridge area adjacent a site on a patients jaw bone ridge for receiving the hole, the bone engagement means being adapted to fix the arrangement on the ridge;

a guide member connected to the bone engagement means and adapted to extend from the bone engagement means over the site, the guide member having a guide channel which has an axis that is aligned with an acceptable axis of the hole to be drilled, the guide channel being shaped to guide a bur for drilling the hole, the guide member defining a closed, cylindrical guide channel; and the bone engagement means comprising a pair jaws, at least one of the jaws being articulated with respect to the other and the jaws being positioned and shaped to engage respective buccal and lingual surfaces of the ridge area of a jaw bone for engaging the jaw bone and fixing the guide member over the ridge of the jaw bone, and means defining a reference surface for engaging the ridge area, which reference surface is substantially in a common plane with a bone engagement surface of the guide member.

18. An implant guide arrangement for use in drilling a hole in an edentulous area of a jaw bone in preparation for receiving a dental implant in the jaw bone, comprising:

bone engagement means adapted to engage a jaw bone ridge area adjacent a site on a patients jaw bone ridge for receiving the hole, the bone engagement means being adapted to fix the arrangement on the ridge;

a guide member connected to the bone engagement means and adapted to extend from the bone engagement means over the site, the guide member having a guide channel which has an axis that is aligned with an acceptable axis of the hole to be drilled, the guide channel being shaped to guide a bur for drilling the hole, the guide member defining a closed, cylindrical guide channel; and an extension for use with the bone engagement means and guide member, said extension comprising a further guide member, a bridge connected to said further guide member and a pin extending from said bridge, said pin having an axis and said guide member having a channel with an axis parallel to said axis of said pin and spaced from said axis of said pin by an amount corresponding to a spacing between implant holes to be drilled into the jaw bone ridge.

* * * * *